United States Patent
Carlsen, Jr.

(10) Patent No.: US 6,185,446 B1
(45) Date of Patent: Feb. 6, 2001

(54) METHOD AND APPARATUS FOR MONITORING THE BREATHING OF A PATIENT DURING MAGNETIC RESONANCE IMAGING

(76) Inventor: William F. Carlsen, Jr., 40108 Highway 49, Suite C286, Oakhurst, CA (US) 93644

(*) Notice: Under 35 U.S.C. 154(b), the term of this patent shall be extended for 0 days.

(21) Appl. No.: 09/138,090

(22) Filed: Aug. 21, 1998

(51) Int. Cl.[7] ................................................ A61B 5/00
(52) U.S. Cl. ................... 600/411; 600/529; 250/458.1
(58) Field of Search ............................... 600/411, 412, 600/418, 421, 529, 532, 537; 250/458.1, 459.1

(56) References Cited

U.S. PATENT DOCUMENTS

| | | | |
|---|---|---|---|
| 3,368,212 | 2/1968 | Klyce | 340/239 |
| 3,884,219 | 5/1975 | Richardson | 128/2 |
| 4,223,226 | 9/1980 | Quick | 250/458 |
| 4,437,772 * | 3/1984 | Samulski | 374/129 |
| 4,621,929 * | 11/1986 | Phillips . | |
| 4,652,143 | 3/1987 | Wickersheim | 374/161 |
| 4,719,424 * | 1/1988 | Jimbo et al. | 324/309 |
| 4,777,963 | 10/1988 | McKenna | 128/724 |
| 4,901,141 * | 2/1990 | Costello | 358/93 |
| 4,994,396 * | 2/1991 | Lefkowitz e tal. . | |
| 5,069,222 | 12/1991 | McDondald | 128/724 |
| 5,190,048 | 3/1993 | Wilkinson | 128/724 |
| 5,291,897 * | 3/1994 | Gastrin et al. | 128/716 |
| 5,323,776 | 6/1994 | Blakeley | 128/633 |
| 5,676,154 * | 10/1997 | Pettersson | 128/719 |

OTHER PUBLICATIONS

Luxtron Sales Literature; Model 1000A Fluoroptic Thermometer; (Nov. 1981); 2 pgs.

Zhang, Zhiyi; Grattan, Kenneth T. V.; Palmer, Andrew W.; SPIE Proceedings vol. 1885; Cr:LiSAF fluorescence lifetime based fiber optic thermometer and its applications in clinical RF heat treatment; (Jan. 1993); 6 pgs.

Leilabady, Akhaven P.; Corke, M.; Optics Letters, vol. 12, No. 10; All–fiber–optic remote sensing of temperature employing interferometic techniques; (Oct. 1987); 3 pgs.

* cited by examiner

*Primary Examiner*—Marvin M. Lateef
*Assistant Examiner*—Shawna J. Shaw (57) ABSTRACT

A breath sensor utilizes optical fibers to detect the flow of a patients respiratory airstream. As it has no conductive or magnetic parts, it can be used on patients within the bore of a magnetic resonance imaging system for simple, safe, and rapid assessment of a patient's breathing.

21 Claims, 5 Drawing Sheets

METHOD AND APPARATUS FOR MONITORING THE BREATHING OF A PATIENT DURING MAGNETIC RESONANCE IMAGING

BACKGROUND

1. Field of Invention

The present invention relates to a method and device for monitoring a patient's breathing during magnetic resonance imaging (MRI).

2. Description of Prior Art

Patients undergoing an MRI exam are generally left isolated in a shielded room during the imaging procedure. When a patient is placed in the bore of the MRI magnet, he or she is nearly completely screened from view. The patient's movements, which are commonly used as indicators of the patient's well-being, are extremely difficult to observe. This creates concerns when imaging patients at risk of untoward complications while within the bore of the magnet.

There are three classes of patients which warrant careful attention during MRI imaging. First, a large percentage of patients develop mild to severe claustrophobia while within the confines of the magnet bore. It is common practice to assess their status by speaking with them over an intercom system. More sophisticated types of monitoring are not considered cost effective for these patients. Second, more serious concerns arise when gadolinium contrast agents are administered, when agents for conscious sedation (such as benzodiazapines or synthetic opiates) are administered, or when patients are heavily sedated. Monitoring of these patients consists generally of a nurse standing by, who intermittently manually checks vital signs. Occasionally, an MRI compatible oxygen saturation monitor is placed on these patients, giving a delayed and nonspecific measure of respiratory status. Third, patients that are medically unstable often require continuous monitoring of primary physiological parameters or they cannot be imaged at all.

In general, a patient's breathing is used as a primary means of assessment. Changes in breathing usually occur in advance of more serious complications evidenced by decreased oxygen saturation, respiratory acidosis, mental agitation and cardiac disturbances including cardiac arrest. Respiration monitoring, however, often appears to be given a secondary role to more sophisticated measurements such as oxygen saturation, blood pressure, or heart rate. This is a holdover from other medical disciplines where the patient is readily accessible and the presence of breathing is usually quite obvious. Students of cardiopulmonary resuscitation (CPR) know that the oxygen saturation, blood pressure, etc. are quite irrelevant when presented with a patient who is not breathing.

Conventional patient monitoring equipment is unsuitable for use in or near an MRI system because: 1) it puts patients at risk for burns due to eddy currents generated within conductive parts, 2) conventional monitoring equipment frequently gives erroneous indications or malfunctions in the presence of the large static and changing magnetic fields, and radio frequency (RF) electric fields generated by an MRI system, and 3) conductive or magnetic parts can cause unacceptable distortion of the diagnostic images.

Within the context of the present invention, the words conductive and magnetic have the following meaning: A part is considered "conductive" if its electrical conductivity is sufficiently high such that the currents induced in said part by the magnetic fields present in an MRI system cause either significant heating within said part or detectable distortion of images of said MRI system. A part is considered "magnetic" if its magnetic susceptibility is sufficiently high or its magnetic permeability is sufficiently different from a value of 1.0 such that detectable distortion of images of said MRI system occurs.

At present, there do exist monitors which have adapted conventional monitoring technology to the MRI environment. For example, U.S. Pat. No. 5,323,776 to Blakely et al (1994) describes an MRI compatible pulse oximetry system. In addition, Invivo Inc. presently sells an MRI compatible system which measures several patient parameters. Both systems, however, make use of conductive parts, making the placement of sensors and associated cabling problematic. In addition, these systems are expensive and complex, and as such are not commonly used outside of the most sophisticated imaging centers and hospitals. At present, many patients who could benefit from MRI imaging are either put at risk for lack of any monitoring, or are ineligible for the procedure for lack of cost effective MRI compatible monitoring equipment.

For certain MRI imaging protocols, there is a need to synchronize the imaging process with the patient's breathing. Motion artifacts in MRI images due to movement of the patient can be reduced by collecting image data at the same point in the patient's respiratory cycle. This is generally accomplished by monitoring chest wall movement with a mechanical transducer wrapped around the patient's chest. Although these chest wall movement sensors are considered adequate for the reduction of motion artifact, they are not suitable for monitoring the patient's exchange of respiratory air. This is because chest wall movement does not necessarily correlate with the exchange of air in a patients lungs. For example, shallow breathers, diaphragm breathers, and emphysematous patients often exhibit small or anomalous chest wall movements as air in their lungs is exchanged. In addition, patient movement unrelated the breathing will falsely trigger these type sensors. Chest wall movement sensors are, therefore, not a reliable monitor of a patients well being. Conversely, a respiration sensor which does sense the exchange of respiratory air may provide a useful signal for respiratory gating. It will be more sensitive to subtle movements of the lungs and insensitive to patient movement unrelated to breathing.

In the absence of large magnetic or RF electric fields, many methods of sensing respiration have been used. One particular class of respiration sensors utilizes a thermistor anemometer placed near the nose and/or mouth of the patient. U.S. Pat. No. 3,368,212 to Klyce (1968) showed that breath flow could be sensed by measuring the temperature of a thermistor placed in the respiratory airstream of a patient. Expired air from the patient's lungs, with it's elevated temperature, causes the thermistor temperature to rise. Inspired air causes the thermistor temperature to fall back toward ambient air temperature. Monitoring the rise and fall of the thermistor temperature gives a measure of the patient's respiration. Several patents have improved on this basic concept by improving placement of the thermistor and the use of other types of temperature sensors. U.S. Pat. No. 3,884,219 to Richardson et al (1975), U.S. Pat. No. 4,777,963 to McKenna (1988), and U.S. Pat. No. 5,190,048 to Wilkinson (1993) are examples of thermistor based breath sensors. U.S. Pat. No. 5,069,222 to McDonald (1991) is an example of a thermocouple based breath sensor. This class of breathing sensor is particularly advantageous in that it measures the actual exchange of air or respiratory flow.

Other methods of detecting the presence of breathing such as chest wall movement or electrical chest wall impedance only infer the movement of respiratory air indirectly.

The large magnetic and RF electric fields present in an MRI system, however, make these breath sensing methods unusable due to image distortion caused by induced magnetic fields of the temperature sensor and associated cabling, heating caused by induced currents in the temperature sensor and associated cabling, and noise induced in the temperature sensor and associated cabling by changing electromagnetic fields. Indeed, any conductive or magnetic part placed in the bore of an MRI system is problematic because of the risk for patient burns, and the potential for image distortion compromising diagnostic quality.

A type of temperature sensor which is potentially unaffected by large magnetic and RF electric fields is a fiberoptic temperature sensor. Such sensors generally comprise an optical exciter and receiver system, a sensor tip which responds optically in some way when its temperature changes, and an optical fiber or fibers which couple the sensor tip to the optical exciter and receiver system. There are many examples of fiberoptic temperature sensors in the prior art. U.S. Pat. No. 4,223,226 to Quick et al (1980) showed that temperature at the end of an optical fiber could be determined by measuring changes in the emissions of a fluorescent phosphor placed at the tip of the optical fiber. U.S. Pat. No. 4,652,143 to Wickersheim et al (1987) demonstrated a fluorescent phosphor based fiberoptic sensor system and incorporated it into a commercial instrument for Luxtron Inc. Zhang et al (1993) demonstrated a fluorescent sensor based on chromium doped lithium strontium aluminum fluoride, which was particularly sensitive at typical physiological temperatures. Leilabady et al (1987) showed that a singlemode optical fiber Fabry-Perot interferometer could be used to measure temperature.

Present commercial implementations of fiberoptic temperature sensors are not suited for breath sensing because: a) they often lack the required response time to follow breathing rates, especially those of hyperventilating patients, children, and neonates, b) they often lack the required sensitivity to resolve the small thermal variations in a patient's respiratory airstream, c) they are designed for very accurate measurement of temperature over a broad range and are thereby excessively costly, d) the sensor tips themselves are relatively expensive and thereby cannot be treated as a disposable item, which is often necessary in the medical environment to minimize the spread contagious disease, e) some devices employ conductive and/or magnetic materials in the sensor tip, mitigating their use in an MRI environment, and f) they lack a sufficiently long optical fiber to span the distance between the operator console and the MRI magnet bore. Thus, none of these implementations anticipate their use for breath monitoring or breath monitoring during MRI imaging.

OBJECTS AND ADVANTAGES

Accordingly, several objects and advantages of the present invention are:

(a) to provide a simple and cost effective way to assess changes in a patient's breathing during an MRI exam, thus forewarning of more serious complications;
(b) to provide a simple and cost effective way to assess a patient's medical status during an MRI exam, thus opening the way to providing MRI imaging to a broader class of patients;
(c) to provide a patient status monitor which contains no conductive or magnetic parts which are in or near the bore of the MRI system, thus mitigating the danger of sensor heating and burns to patients caused by induced currents;
(d) to provide a patient status monitor which contains no conductive or magnetic parts which are in or near the bore of the MRI system, thus mitigating any possibility of image distortion due to induced magnetic fields in the sensor;
(e) to provide a patient status monitor who's sensor tip end can be widely separated from its output display, such that said display can be placed near an MRI operators console, well away from the influence of the electric and magnetic fields found near the bore of an MRI system;
(f) to provide a simple and cost effective way to follow a patient's breathing during an MRI exam, thus providing a signal useful for respiratory gating of MRI signals;
(g) to provide a patient status monitor which is useful in other settings, besides MRI, where the patient is not directly accessible; and
(h) to provide a patient status monitor which is unaffected by external electric and magnetic fields which are often present during procedures other than MRI, such as cardiac defibrillation, electrocautery, or RF diathermy.

REFERENCE NUMERALS IN DRAWINGS

| | |
|---|---|
| 10 optical exciter | 11 MRI magnet bore |
| 12 optical transmission means | 13 temperature change sensing tip |
| 14 patient | 15 optical receiver |
| 16 processor | 17 display |
| 40 clock | 41 current source |
| 42 excitation source | 43 filter |
| 44 optical fiber | 45 beamsplitter |
| 46 MRI magnet bore | 47 temperature change sensing tip |
| 48 Cr:LiSAF | 49 optical adhesive |
| 50 blocking filter | 51 photodiode |
| 52 amplifier | 53 limiter |
| 54 phase detector | 55 analog to digital converter |
| 56 processor | 57 display |
| 60 current source | 61 singlemode diode laser |
| 62 singlemode optical fiber | 63 directional coupler |
| 64 MRI magnet bore | 65 temperature change sensing tip |
| 66 multimode optical fiber | 67 reflector |
| 68 reflector | 69 photodiode |
| 70 amplifier | 71 counter |
| 72 processor | 73 display |
| 80 current source | 81 diode laser |
| 82 singlemode optical fiber | 83 directional coupler |
| 84 MRI magnet bore | 85 temperature change sensing tip |
| 86 singlemode optical fiber | 87 reflector |
| 88 reflector | 89 photodiode |
| 90 amplifier | 91 counter |
| 92 processor | 93 display |

SUMMARY OF THE INVENTION

It is an object of the present invention to provide an optical method and apparatus for detecting the presence of breathing in patients in the presence of electric and magnetic fields such as those found in the bore of a magnetic resonance imaging system.

This is accomplished using a fiberoptic based temperature change sensing tip which is placed in the respiratory airstream of a patient (typically near the nose, mouth, tracheal tube, or endotracheal tube if intubated). The temperature change sensing tip is excited by an optical signal transferred down an optical fiber from an excitation source. The temperature change sensing tip and optical fiber comprise no conductive or magnetic parts. The excitation source is placed away from the strong magnetic and RF electric fields of the bore of the MRI system. As the patient breathes, temperature changes are induced in the temperature change sensing tip by the patient's expiration of warm air, and by the patient's inspiration of ambient air. The temperature change sensing tip has sufficiently low thermal mass so that its response time is short and can follow breathing induced temperature changes. The temperature change sensing tip responds optically to these changes in temperature, and an optical signal reflecting these changes is transferred down either the same optical fiber or a separate optical fiber away from the bore of the MRI system. The temperature change sensing tip needs only detect changes in temperature. The measurement of the actual temperature is unneeded to establish the existence of respiratory air flow.

Away from the bore of the MRI system, the optical signal is converted to an electrical signal. Changes in temperature of the temperature change sensing tip are then determined from the electrical signal. These temperature changes are analyzed and used to infer the presence of breathing. This information is then displayed for a physician or technologist doing the exam; the presence of breathing and respiration rate being used as a first indicator of patient well-being.

DESCRIPTION OF THE INVENTION

Figure 1:
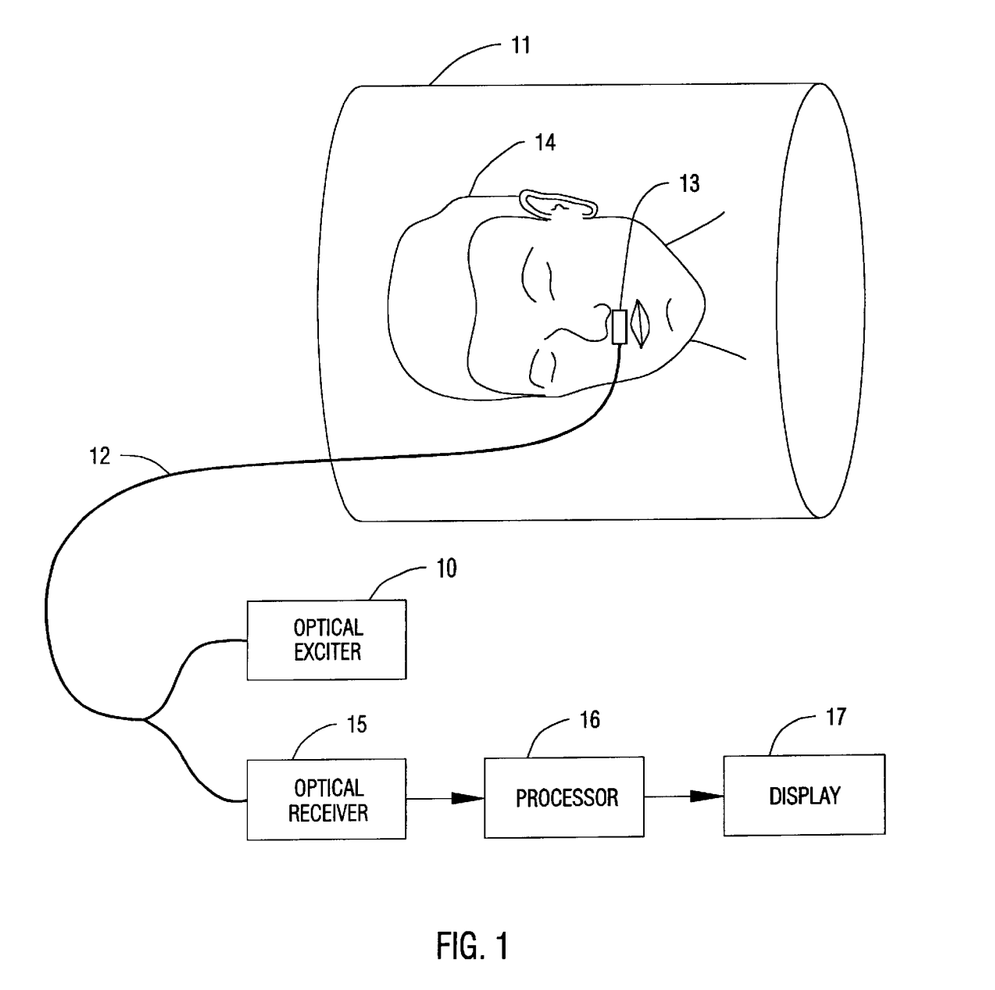
FIG. 1 shows a generalized fiberoptic breath sensing system.

A generalized version of the present invention is illustrated in FIG. 1. An optical exciter 10 located away from an MRI magnet bore 11, sends an excitation light down an optical transmission means 12 consisting of one or more optical fibers, said optical transmission means going into MRI magnet bore 11, and thence to a temperature change sensing tip 13. A patient 14 is located inside MRI magnet bore 11. Temperature change sensing tip 13 is placed in the respiratory airstream of patient 14. Temperature change sensing tip 13 and those parts of optical transmission means 12 within MRI magnet bore 11 comprise materials which are substantially non-conductive and nonmagnetic. Blood pumped from patient 14's heart through the pulmonary artery and thence to the alveoli of the lungs, warms the air in the patient's lungs. As patient 14 breathes, thermal changes are induced in temperature change sensing tip 13 by the patient's expiration of warm air from his or her lungs, and by the patient's inspiration of ambient air. Temperature change sensing tip 13 receives the excitation light, and then in response to the breathing induced temperature changes, produces a return light back down optical transmission means 12, away from MRI magnet bore 11, to an optical receiver 15, where the return light is converted into an electrical signal, and thence input to a processor 16 which computes the temperature changes at temperature change sensing tip 13 and then outputs the resultant breathing information to a display 17, showing an indication of the patient's breathing for a physician or technologist doing the exam.

PREFERRED EMBODIMENTS

Figure 2:
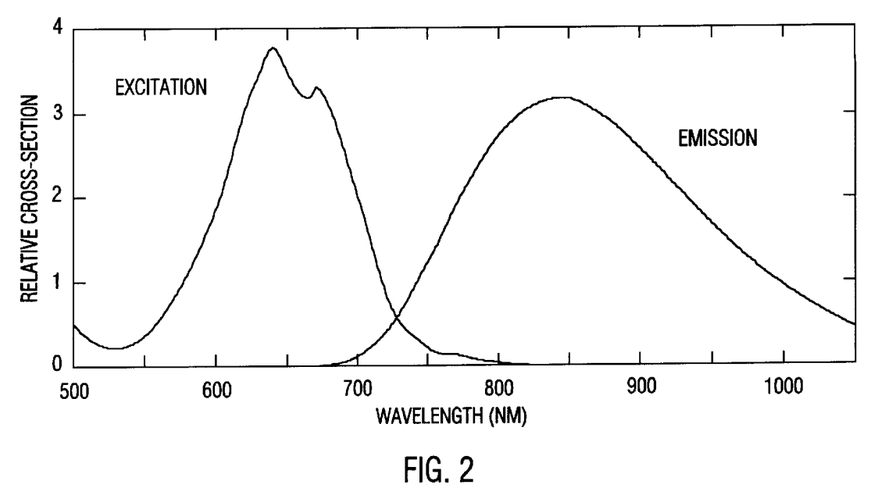
FIG. 2 shows the fluorescence excitation and emission spectra of Cr:LiSAF.
Figure 3:
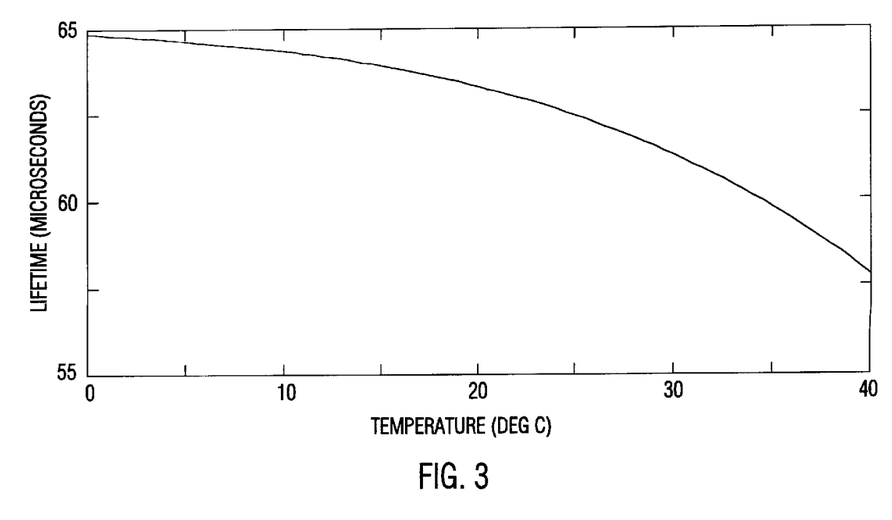
FIG. 3 shows the fluorescence lifetime verses temperature of Cr:LiSAF.

The first preferred embodiment of this invention is a fiberoptic breathing sensor made with a temperature change sensing tip comprising a fluorescence material which changes its fluorescence lifetime with temperature. One such luminescent material is Cr:LiSAF. Cr:LiSAF is the colquerite crystal lithium strontium aluminum fluoride (LiSrAlF$_6$) doped with chromium ions (Cr$^{3+}$). The Cr$^{3+}$ ions substitute for aluminum ions in the crystal. The fluorescence excitation and emission spectra for Cr:LiSAF are shown in FIG. 2. With a doping level of 1% Cr$^{3+}$ (that is, 1% of the Al ions are substituted with Cr$^{3+}$ ions), Cr:LiSAF has a fluorescence lifetime (l/e) of approximately 61 microseconds at a temperature of approximately 30 degrees Celsius, as illustrated in FIG. 3. The variation in the fluorescence lifetime with temperature at 30 degrees Celsius is approximately 266 nanoseconds/deg Celsius. This material is available from VLOC, a Subsidiary of II-VI Incorporated, New Port Richey, Fla.

Figure 4:
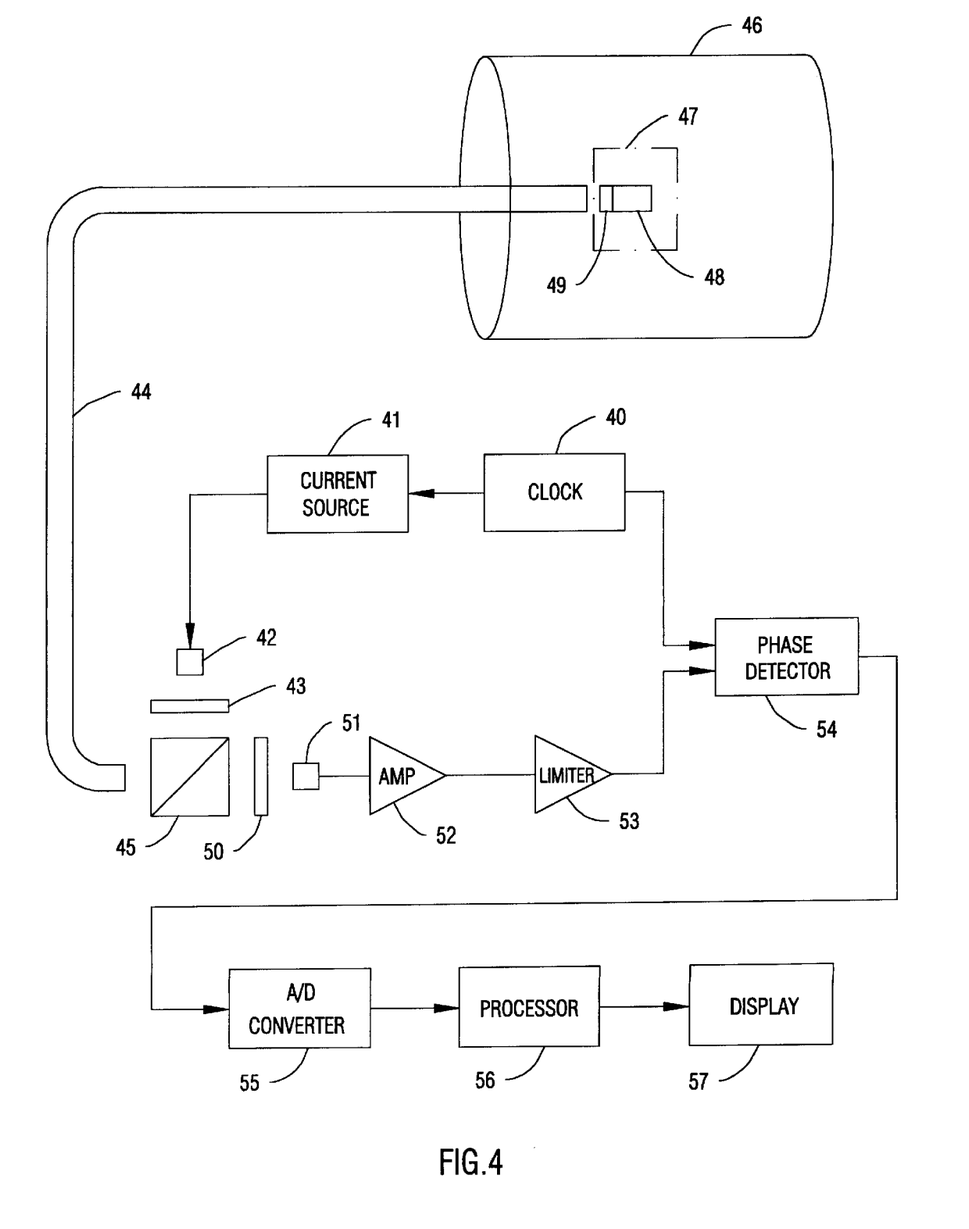
FIG. 4 shows a preferred embodiment using fluorescence temperature sensing.

A block diagram of the system is shown in FIG. 4. A clock 40 generates a signal of a fixed frequency $f$, which modulates a current source 41, driving an excitation source 42. Excitation source 42 comprises a light emitting diode (LED) or laser diode. The output wavelength of excitation source 42 is chosen to approximately match the absorption band of Cr:LiSAF near 675 nanometers (nm), illustrated in FIG. 2. The light from excitation source 42 is amplitude $$f = \frac{1}{2\pi\tau_r} \tag{1}$$

modulated with a continuous wave (CW) signal at frequency $f$, where:
and where $\tau_r$ is the fluorescence lifetime of Cr:LiSAF at a desired reference temperature. Excitation light from excitation source 42 is transmitted through a filter 43 which rejects light from excitation source 42 having wavelengths longer than 750 nm. Excitation light is thence coupled to an optical fiber 44 via a beamsplitter 45. Optical fiber 44 carries the excitation light into the bore of an MRI magnet bore 46, where a patient is located.

A temperature change sensing tip 47, comprising a small amount of Cr:LiSAF 48, and an optical adhesive 49 is attached to the end of optical fiber 44. The smaller the temperature change sensing tip 47, the less it's thermal mass, and thus the faster it's response time. A risetime (l/e) of approximately 1 second will adequately track an adult patient's breathing, while a risetime of approximately 100 milliseconds is adequate for tracking a neonatal or a pediatric patient's breathing. As the temperature change sensing tip 47 is made smaller, however, the fluorescent signal decreases. This can be compensated for by increasing the Cr$^{3+}$ concentration in Cr:LiSAF 48.

When optically excited as described above, Cr:LiSAF 48 emits a fluorescent light in a wavelength band peaking near 850 nm, as illustrated in FIG. 2. The fluorescent light is CW amplitude modulated at frequency $f$. The phase of the fluorescent light amplitude modulation, however, is shifted relative to the phase of the excitation light amplitude modulation. This relative phase-shift, $\phi$, is related to the fluorescent lifetime of the Cr:LiSAF by $$\phi = \tan^{-1}(2\pi f \tau) \tag{2}$$

where $\tau$ is the fluorescent lifetime at the current temperature of the Cr:LiSAF.

Temperature change sensing tip 47 and those parts of optical fiber 44 within MRI magnet bore 46 comprise materials which are substantially non-conductive and non-magnetic. Temperature change sensing tip 47 is placed in the respiratory airstream of the patient.

Return light, consisting of a portion of this phase-shifted fluorescent light, is coupled back down optical fiber 44, out of and away from MRI magnet bore 46, where it is separated optically from the excitation light with beam splitter 45 and a blocking filter 50 which blocks excitation light wavelengths. Return light is thence detected with a photodiode 51. The detected signal is amplified in an amplifier 52, then input to a limiter 53 to remove amplitude variations, then fed into one input of a phase detector 54. The CW signal from clock 40, which is used to drive current source 41, is also fed into the other input of phase detector 54. The output of phase detector 54 is a voltage which varies approximately with the relative phase between the amplitude modulation of the excitation and emission optical signals. An analog to digital converter 55 converts the voltage output from phase detector 54 to a digital signal which is input to a processor 56. Processor 56 converts this relative phase signal into temperature changes at temperature change sensing tip 47, and from this computes a breathing signal which is input to a display 57.

Figure 5:
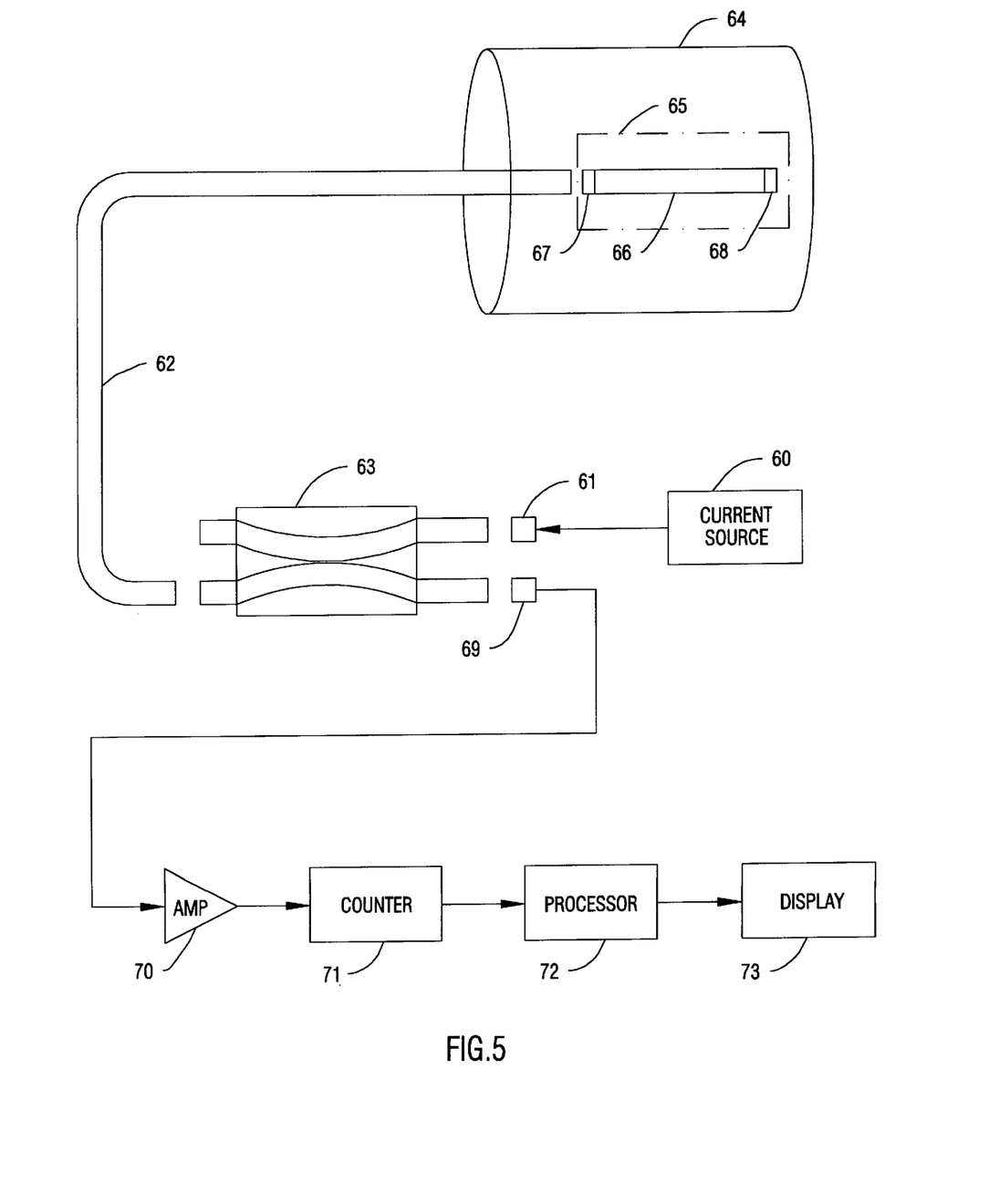
FIG. 5 shows a preferred embodiment using multimode optical fiber temperature sensing.

A second preferred embodiment of this invention is a fiberoptic breathing sensor comprising a multimode fiberoptic speckle interferometer, illustrated in FIG. 5. A current source 60 excites a singlemode diode laser 61. The wavelength of singlemode diode laser 61 is 830 nm, chosen primarily on the basis of cost. Excitation light from singlemode diode laser 61 is coupled into a singlemode optical fiber 62 via a directional coupler 63. Singlemode optical fiber 62 is an optical fiber which has a sufficiently small core diameter such that only a single transverse optical mode will propagate in said optical fiber at the chosen laser wavelength of 830 nm. Singlemode optical fiber 62 carries the excitation light into an MRI magnet bore 64, where a patient is located. Excitation light from singlemode optical fiber 62 is coupled into a temperature change sensing tip 65 comprising a length of a multimode optical fiber 66 which has two optical reflectors 67 and 68 at each end. Reflectors 67 and 68 could consist of the intrinsic Fresnel reflection of multimode optical fiber 66 or be enhanced by the addition of coatings. The diameter of multimode optical fiber 66 is chosen such that a plurality of transverse optical modes will propagate in the multimode optical fiber at the chosen laser wavelength of 830 nm.

Breathing, causes changes in the temperature of temperature change sensing tip 65, thus causing changes in the transit time of the light between reflectors 67 and 68 (either by index changes or mechanical changes). Light reflects off reflectors 67 and 68 and circulates in multimode optical fiber 66 between reflectors 67 and 68, interfering over many round trips. Since multimode optical fiber 66 supports a plurality of axial optical modes, a plurality of roundtrip paths are excited, creating a plurality of interferences (speckle). The length of multimode optical fiber 66 is chosen so that it gives multiple countable interferences over the course of a typical breath of a patient.

Temperature change sensing tip 65 and those parts of optical fiber 62 within MRI magnet bore 64 comprise materials which are substantially non-conductive and non-magnetic. Temperature change sensing tip 65 is placed in the respiratory airstream of the patient.

Return light, consisting of some of the circulating light which is reflected from each reflector 67 and 68, is coupled back down singlemode optical fiber 62, out of and away from MRI magnet bore 64, to directional coupler 63. Directional coupler 63 separates the return light reflected from temperature change sensing tip 65 and the excitation light from diode laser 61. The return light is directed to a photodiode 69 where the interferences coupled from temperature change sensing tip 65 produce a plurality of light to dark transitions during each breath. The signal produced by photodiode 69 is input to an amplifier 70 and thence to a counter 71, where the light to dark transitions are counted. The count rate from counter 71 is input to a processor 72. The mean frequency of this fluctuating signal is a function of the change in transit time of the light circulating in temperature change sensing tip 65, thus following the change in the temperature of temperature change sensing tip 65. Processor 72 integrates this temperature change signal to obtain the relative temperature of temperature change sensing tip 65. This relative temperature is then converted by processor 72 to a breathing signal which is input to a display 73.

Figure 6:
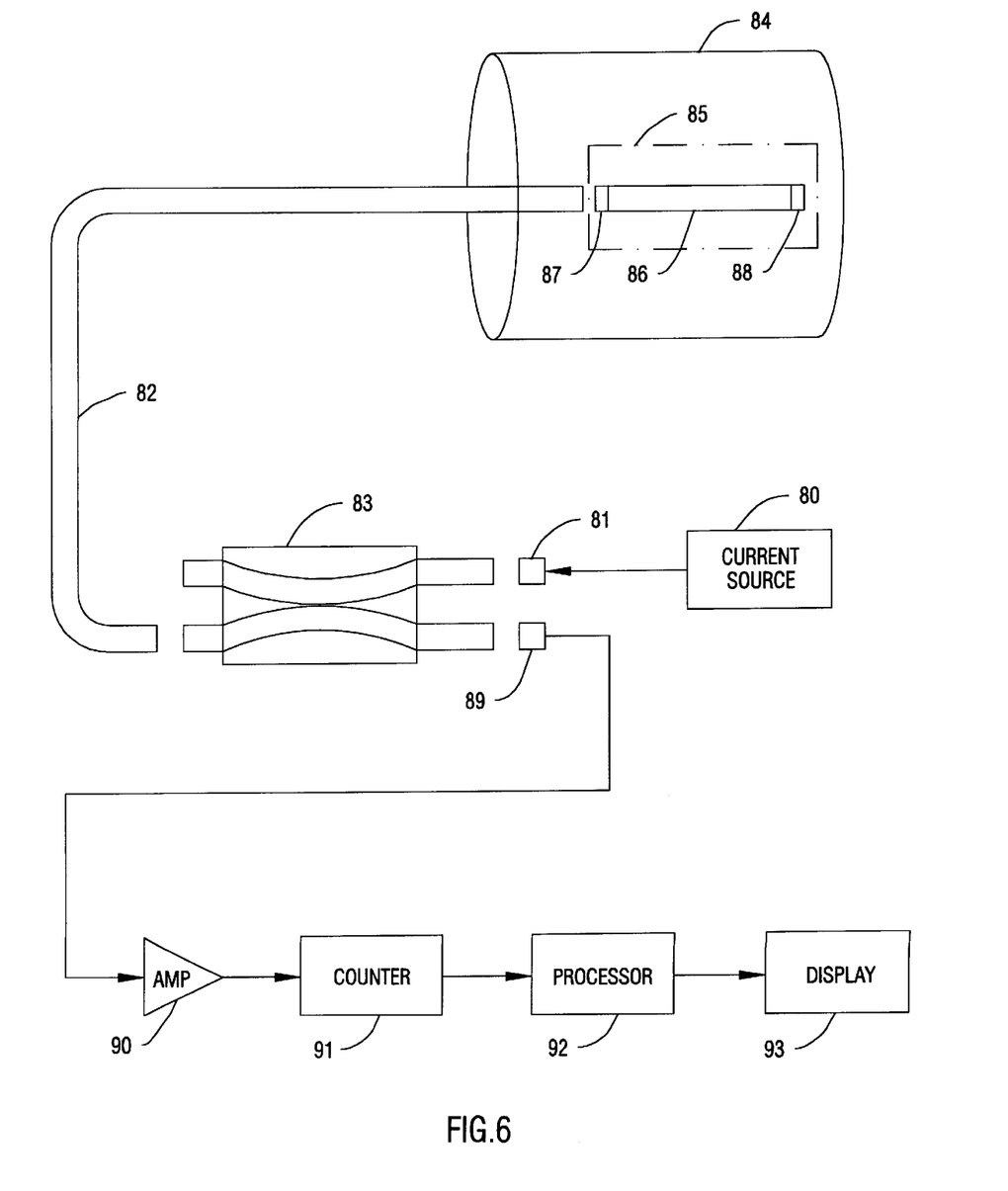
FIG. 6 shows a preferred embodiment using singlemode optical fiber temperature sensing.

A third preferred embodiment of this invention is a fiberoptic breathing sensor comprising a singlemode fiberoptic Fabry-Perot interferometer, illustrated in FIG. 6. Current source 80 excites singlemode diode laser 81. The wavelength of diode laser 81 is 830 nm, chosen primarily on the basis of cost. Excitation light from diode laser 81 is coupled into a singlemode optical fiber 82 via a directional coupler 83. Singlemode optical fiber 82 is an optical fiber which has a sufficiently small core diameter such that only a single transverse optical mode will propagate in said optical fiber at the chosen laser wavelength of 830 nm. Singlemode optical fiber 82 carries the excitation light into an MRI magnet bore 84, where a patient is located. Excitation light from singlemode optical fiber 82 is coupled into a temperature change sensing tip 85 comprising a second length of singlemode optical fiber 86 which has two optical reflectors 87 and 88 at each end. Reflectors 87 and 88 could consist of the intrinsic Fresnel reflection of singlemode optical fiber 86 or be enhanced by the addition of coatings.

Breathing, causes changes in the temperature of temperature change sensing tip 85, thus causing changes in the transit time of the light between reflectors 87 and 88 (either by index changes or mechanical changes). Light reflects off reflectors 87 and 88 and circulates in singlemode optical fiber 86, between reflectors 87 and 88, interfering over many round trips. The length of singlemode optical fiber 86 is chosen so that multiple countable interference modulations occur over the course of a typical breath of a patient.

Temperature change sensing tip 85 and those parts of optical fiber 82 within MRI magnet bore 84 comprise materials which are substantially non-conductive and non-magnetic. Temperature change sensing tip 85 is placed in the respiratory airstream of the patient. Return light, consisting of some of the circulating light which is reflected from each reflector 87 and 88, is coupled back down the first singlemode optical fiber 82, out of and away from MRI magnet bore 84, to directional coupler 83. Directional coupler 83 separates the return light from temperature change sensing tip 85 and the excitation light from diode laser 81. The return light is directed to a photodiode 89. Interference of the return light reflected from reflectors 87 and 88 produces a plurality of light to dark transitions (temporal fringes) at photodiode 89 during each breath. The signal produced by photodiode 89 is input to an amplifier 90, and thence to a counter 91, where the light to dark transitions are counted. The count rate from counter 91 is input to a processor 92. This count rate is a function of the change in transit time of the light circulating in temperature change sensing tip 85, and thus the change in the temperature of temperature change sensing tip 85. Processor 92 integrates this signal to obtain the relative temperature of temperature change sensing tip 85. This relative temperature is then converted by processor 92 to a breathing signal which is input to a display 93. Note that this differs from the usual singlemode optical fiber temperature sensor in that only changes in temperature are required to infer the presence of breathing. The usual complications of determining the absolute fringe count and the direction of the fringe movement (and thereby the actual temperature) and are not required.

Conclusions, Ramifications, and Scope of Invention

Thus the reader will see that the present invention provides a new, simple, and potentially low cost way of monitoring a patient while undergoing an MRI exam. It monitors a primary indicator of patient well being, his or her breathing. It does this in a way that gives a direct indication of actual air exchange in the lungs, rather than indirectly with electrical or mechanical signals such as chest wall impedance or movement. This is accomplished using no electrically conductive or magnetic parts, thus mitigating problems associated with patient safety, the quality of the MRI images, and the quality of the monitored signal itself, normally associated with other existing monitoring modalities.

While the above description contains many specificities, these should not be construed as limitations on the scope of the invention, but rather as an exemplification of the preferred embodiments thereof. Many other variations are possible. For example:

(a) in the first preferred embodiment, other fluorescent or luminescent materials which exhibit a temperature dependent luminescence could be used; or (b) in the first preferred embodiment, the Cr:LiSAF could be in the form of a single crystal, or a polycrystalline solid, or a granulated powder; or (c) in the first preferred embodiment, the phase angle between excitation and emission light modulations could be held constant by varying the frequency $f$ of the excitation light modulation as the temperature change sensing tip temperature varies. The temperature change sensing tip temperature could then be inferred from the frequency of the excitation modulation; or (d) in the first preferred embodiment, the fluorescent lifetime could be inferred in other ways such as using an excitation light pulse and measuring the resultant decay of the emission light, or measuring the relative amplitudes of the excitation and emission light; or (e) in all three preferred embodiments, separate optical fibers could be used to transmit the excitation and return light respectively; or (f) in the second and third preferred embodiments, the singlemode optical fiber from the excitation source to the temperature change sensing tip need not be strictly singlemode. It must only generate sufficiently low modal noise such that the temperature change induced modulations from the temperature change sensing tip itself are not obscured; or (g) in the second preferred embodiment, the excitation light source need not be strictly a singlemode laser. It must only have sufficiently narrow optical bandwidth such that the contrast between speckles is sufficient to detect temperature changes in the temperature change sensing tip; or (h) in the second preferred embodiment, the return light could be carried by a separate multimode fiber for better signal to noise performance; or (i) in the second preferred embodiment, the temperature change sensing tip need not comprise a multimode optical fiber per se, but any optical cavity which supports multiple transverse optical modes, where the optical pathlengths for these transverse optical modes change with temperature, and where the resultant interference (speckle) modulations can be coupled into a return optical fiber; or (j) in the third preferred embodiment, the light to dark modulation of the return light seen by the photodiode need not occur multiple times during a breath. Observation of the amplitude of a single fringe is sufficient to infer temperature changes at the temperature change sensing tip; or (k) in all three preferred embodiments, the breathing signal could also be used for respiratory gating of MRI signals for reducing motion artifact; or (l) use of the present invention for monitoring breathing, is not limited exclusively to MRI procedures, but could also be applicable in other procedures and situations where external electric and magnetic fields are problematic.

Accordingly, the scope of the invention should be determined not by the embodiments illustrated, but by the appended claims and their legal equivalents.

What is claimed is:

1. A method to detect the presence of breathing of a patient, comprising:

(a) providing an optical exciter means which generates an excitation light, (b) providing an optical transmission means comprising one or more optical fibers, (c) transmitting said excitation light through said optical transmission means, (d) providing an optical temperature change sensing means which, when excited with said excitation light, generates a return light, and where said return light changes characteristics correspondent with changes in the temperature of said optical temperature change sensing means, (e) coupling the transmitted excitation light from said optical transmission means into said optical temperature change sensing means, (f) placing said optical temperature change sensing means in thermal communication with the respiratory airstream of said patient, (g) transmitting said return light through said optical transmission means, (h) providing an optical receiver means which converts said return light into an electrical signal, (i) coupling said return light out of said optical transmission means into said optical receiver means, whereby said electrical signal indicates the presence of breathing of said patient.

2. A method to detect the presence of breathing of a patient within the bore of a magnetic resonance imaging system, comprising:

(a) providing an optical exciter means which generates an excitation light, (b) providing an optical transmission means comprising one or more optical fibers and comprising substantially non-conductive and substantially non-magnetic materials in those parts of said optical transmission means placed within the bore of said magnetic resonance imaging system, (c) transmitting said excitation light through said optical transmission means, (d) providing an optical temperature change sensing means which, when excited with said excitation light, generates a return light, where said return light changes characteristics correspondent with changes in the temperature of said optical temperature change sensing means, and where said optical temperature change sensing means consists of substantially non-conductive and substantially non-magnetic materials, (e) coupling the transmitted excitation light from said optical transmission means into said optical temperature change sensing means, (f) placing said optical temperature change sensing means in thermal communication with the respiratory airstream of said patient, (g) transmitting said return light through said optical transmission means, (h) providing an optical receiver means which converts said return light into an electrical signal, (i) coupling said return light out of said optical transmission means into said optical receiver means, whereby said electrical signal indicates the presence breathing of said patient without distorting the magnetic field or gradient fields within said patient, and without the potential for injury of said patient from induced currents.

3. The method in claim 2 wherein said optical temperature change sensing means comprises a luminescent material where said luminescent material is characterized by emitting luminescent radiation when excited by transient optical radiation, and where said luminescent radiation continues and decays in time beyond the cessation of excitation, and said luminescent radiation decays with a functional form which varies in response to variations in the temperature of said luminescent material.

4. The method in claim 3 wherein said luminescent material is chromium doped lithium strontium aluminum fluoride.

5. The method in claim 3 wherein said excitation light is a periodic train of intensity variations of light, and said return light is thereby a periodic train of intensity variations of light, and where the relative phase of the amplitude variations between said excitation light and said return light is a function of the temperature of said luminescent material.

6. The method in claim 3 wherein said excitation light is a transient pulse of light and said return light is thereby another transient pulse of light, and where the decay rate of said return light is a function of the temperature of said luminescent material.

7. The method in claim 3 wherein said excitation light is continuous amplitude light and said return light is thereby of continuous amplitude, and where the amplitude of said return light is a function of the temperature of said luminescent material.

8. The method in claim 2 wherein the variations in temperature of said optical temperature change sensing means due to breathing of said patient are used to derive a respiration rate of said patient.

9. The method in claim 2 wherein the variations in temperature of said optical temperature change sensing means due to breathing of said patient are used to derive a respiratory volume of said patient.

10. The method in claim 2 wherein the variations in temperature of said optical temperature change sensing means due to breathing of said patient are used to derive an inspiratory and an expiratory flow rate of said patient.

11. The method in claim 2 wherein the variation in temperature of said optical temperature change sensing means due to breathing of said patient are used for respiratory gating of signals of said magnetic resonance imaging system.

12. The method in claim 2 wherein:
(a) said optical transmission means comprises at least one singlemode optical fiber, and
(b) said optical temperature change sensing means comprises a multimode optical fiber, and
(c) said multimode optical fiber has sufficient optical reflectivity at its ends to create interference of light within said multimode optical fiber, and
(d) said optical exciter means is an optical source with sufficiently narrow optical bandwidth such that a plurality of intensity fluctuations are observed at said optical receiver means, and where said intensity fluctuations are correlated with the breathing of said patient.

13. The method in claim 2 wherein:
(a) said optical transmission means comprises at least one singlemode optical fiber, and
(b) said optical temperature change sensing means comprises an optical cavity, where said optical cavity can contain a plurality of transverse optical modes, and
(c) said optical cavity has sufficient optical reflectivity at its ends to cause interference of light within said optical cavity, and
(d) said optical exciter means is an optical source with sufficiently narrow optical bandwidth such that a plurality of intensity fluctuations of said return light are observed at said optical receiver means, and where said intensity fluctuations are correlated with the breathing of said patient.

14. The method in claim 2 wherein:
(a) said optical transmission means comprises at least one singlemode optical fiber, and
(b) said optical temperature change sensing means comprises a second singlemode optical fiber, and
(c) said second singlemode optical fiber has sufficient optical reflectivity at each of its ends to create interference of light within said optical temperature change sensing means, and
(d) said optical exciter means is an optical source with sufficiently narrow optical bandwidth such that a change in intensity of said return light is observed at said optical receiver means, and where said change in intensity is correlated with the breathing of said patient.

15. A device for detecting the presence of breathing of a patient within the bore of a magnetic resonance imaging system, comprising:
(a) an optical exciter means which generates an excitation light, where said excitation light comprises certain wavelengths of light sufficient to excite luminescence in a luminescent material;
(b) an optical transmission means comprising one or more optical fibers and comprising substantially non-conductive and substantially non-magnetic materials in those parts of said optical transmission means placed within the bore of said magnetic resonance imaging system, said optical transmission means being attached to one end of said optical exciter means such that said excitation light is coupled into said optical transmission means;
(c) an optical temperature change sensing means:
  (1) comprising said luminescent material which is characterized by emitting luminescent radiation when excited by transient optical radiation, and where said luminescent radiation continues and decays in time beyond the cessation of excitation, and said luminescent radiation decays with a functional form which varies in response to variations in temperature, and (2) comprising an attachment means which holds said luminescent material in sufficiently close proximity to an end of said optical transmission means such that said luminescent material can be excited by said excitation light, and said luminescent radiation is coupled into said optical transmission means, and (3) where said optical temperature change sensing means is placed in thermal communication with said patient's respiratory airstream, and (4) where said optical temperature change sensing means has sufficiently low thermal mass so that it's temperature can be used to follow said patient's breathing; and (d) an optical receiver means which is attached to an end of said optical transmission means such that said luminescent radiation is coupled into said optical receiver means, and where said optical receiver means converts said luminescent radiation into an electrical signal;

whereby said electrical signal indicates the presence of breathing in said patient without distorting the magnetic field or gradient fields within said patient, and without the potential for injury of said patient from induced currents.

16. A device as in claim 15 wherein said luminescent material is chromium doped lithium strontium aluminum fluoride.

17. A device as in claim 15 wherein said excitation light is a periodic train of intensity variations of light, and said luminescent radiation is thereby a periodic train of intensity variations of light, and where the relative phase of the amplitude variations between said excitation light and said luminescent radiation is a function of the temperature of said luminescent material.

18. A device as in claim 15 wherein said excitation light is a transient pulse of light and said luminescent radiation is thereby another transient pulse of light, and where the decay rate of said luminescent radiation is a function of the temperature of said luminescent material.

19. A device for detecting the presence of breathing of a patient within the bore of a magnetic resonance imaging system, comprising:

(a) an optical exciter means which generates an excitation light, where said excitation light has a narrow optical bandwidth;

(b) an optical transmission means comprising at least one singlemode optical fiber and comprising substantially non-conductive and substantially non-magnetic materials in those parts of said optical transmission means placed within the bore of said magnetic resonance imaging system, said optical transmission means being attached to one end of said optical exciter means such that said excitation light is coupled into said optical transmission means;

(c) an optical temperature change sensing means:
   (1) comprising a multimode optical fiber, where said multimode optical fiber can support a plurality of transverse optical modes, and where said multimode optical fiber has sufficient optical reflectivity at its ends to create interference of light within said multimode optical fiber, and
   (2) comprising an attachment means which holds said multimode optical fiber in sufficiently close proximity to an end of said optical transmission means such that the excitation light from said optical transmission means is coupled into said multimode optical fiber such that a plurality of transverse optical modes are excited, and such that a return light consisting of some of the light from said transverse optical modes is coupled into said optical transmission means, and
   (3) where said optical temperature change sensing means is placed in thermal communication with said patient's respiratory airstream, and
   (4) where said optical temperature change sensing means has sufficiently low thermal mass so that it's temperature can be used to follow said patient's breathing; and (d) an optical receiver means which is attached to an end of said optical transmission means such that said return light is coupled into said optical receiver means, and where said optical receiver means converts said return light into an electrical signal, and where said optical bandwidth of said excitation light is sufficiently narrow such that a plurality of intensity fluctuations of said return light are observed at said optical receiver means for each breath of said patient;

whereby said electrical signal indicates the presence of breathing in said patient without distorting the magnetic field or gradient fields within said patient, and without the potential for injury of said patient from induced currents.

20. A device for detecting the presence of breathing of a patient within the bore of a magnetic resonance imaging system, comprising:

(a) an optical exciter means which generates an excitation light, where said excitation light has a narrow optical bandwidth;

(b) an optical transmission means comprising at least one singlemode optical fiber and comprising substantially non-conductive and substantially non-magnetic materials in those parts of said optical transmission means placed within the bore of said magnetic resonance imaging system, said optical transmission means being attached to one end of said optical exciter means such that said excitation light is coupled into said optical transmission means;

(c) an optical temperature change sensing means:
   (1) comprising an optical cavity, where said optical cavity can support a plurality of transverse optical modes, and where said optical cavity has sufficient optical reflectivity at its ends to create interference of light within said optical cavity, and
   (2) comprising an attachment means which holds said optical cavity in sufficiently close proximity to an end of said optical transmission means such that the excitation light from said optical transmission means is coupled into said optical cavity such that said transverse optical modes are excited, and such that a return light consisting of some of the light from said transverse optical modes is coupled into said optical transmission means, and
   (3) where said optical temperature change sensing means is placed in thermal communication with said patient's respiratory airstream, and
   (4) where said optical temperature change sensing means has sufficiently low thermal mass so that it's temperature can be used to follow said patient's breathing; and (d) an optical receiver means which is attached to an end of said optical transmission means such that said return light is coupled into said optical receiver means, and where said optical receiver means converts said return light into an electrical signal, and where said optical bandwidth of said excitation light is sufficiently narrow such that a plurality of intensity fluctuations of said return light are observed at said optical receiver means for each breath of said patient;

whereby said electrical signal indicates the presence of breathing in said patient without distorting the magnetic field or gradient fields within said patient, and without the potential for injury of said patient from induced currents.

21. A device for detecting the presence of breathing of a patient within the bore of a magnetic resonance imaging system, comprising:

(a) an optical exciter means which generates an excitation light, where said excitation light has a narrow optical bandwidth;

(b) an optical transmission means comprising at least one singlemode optical fiber and comprising substantially non-conductive and substantially non-magnetic materials in those parts of said optical transmission means placed within the bore of said magnetic resonance imaging system, said optical transmission means being attached to one end of said optical exciter means such that said excitation light is coupled into said optical transmission means;

(c) an optical temperature change sensing means:
  (1) comprising a singlemode optical fiber having sufficient optical reflectivity at its ends to create interference of light within said singlemode optical fiber, and
  (2) comprising an attachment means which holds said singlemode optical fiber in sufficiently close proximity to an end of said optical transmission means such that the excitation light from said optical transmission means is coupled into said singlemode optical fiber and such that a return light consisting of some of the light reflected from said singlemode optical fiber is coupled into said optical transmission means, and
  (3) where said optical temperature change sensing means is placed in thermal communication with said patient's respiratory airstream, and
  (4) where said optical temperature change sensing means has sufficiently low thermal mass so that it's temperature can be used to follow said patient's breathing; and (d) an optical receiver means which is attached to an end of said optical transmission means such that said return light is coupled into said optical receiver means, and where said optical receiver means converts said return light into an electrical signal, and where said optical bandwidth of said excitation light is sufficiently narrow such that a change in intensity of said return light is observed at said optical receiver means, and where said change in intensity is correlated with the breathing of said patient, whereby said electrical signal indicates the presence of breathing in said patient without distorting the magnetic field or gradient fields within said patient, and without the potential for injury of said patient from induced currents.

* * * * *